(12) United States Patent
Raines (10) Patent No.: US 10,933,231 B2
(45) Date of Patent: Mar. 2, 2021

(54) LEAD INSERTION TOOL

(71) Applicant: ADVANCED NEUROMODULATION SYSTEMS, INC., Plano, TX (US)

(72) Inventor: Aaron Raines, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 180 days.

(21) Appl. No.: 16/147,146

(22) Filed: Sep. 28, 2018

(65) Prior Publication Data

US 2019/0030319 A1  Jan. 31, 2019

Related U.S. Application Data

(63) Continuation of application No. 15/241,866, filed on Aug. 19, 2016, now abandoned.

(51) Int. Cl.
 *A61N 1/372* (2006.01)
 *A61N 1/05* (2006.01)

(52) U.S. Cl.
 CPC ............ *A61N 1/05* (2013.01); *A61N 1/372* (2013.01)

(58) Field of Classification Search
 CPC ... A61N 1/05; A61N 1/056; A61N 2001/0578
 See application file for complete search history.

(56) References Cited

U.S. PATENT DOCUMENTS 5,456,699 A * 10/1995 Armstrong ............... A61N 1/05
606/108

\* cited by examiner

*Primary Examiner* — Allen Porter (57) ABSTRACT

Disclosed herein is a lead insertion tool for inserting a lead connector end of an implantable lead into a lead receptacle of a header of an implantable pulse generator, the implantable lead including a lead body extending distally from the lead connector end. The tool includes a lead pathway and an engagement mechanism. The lead pathway extends through the tool and is configured to receive the implantable lead. The engagement mechanism includes an engaged state and a self-biasing non-engaged state. When the engagement mechanism is self-biased into the non-engaged state, the implantable lead is free to displace along the lead pathway. When the engagement mechanism is forced into the engaged state, the lead cannot displace along the lead pathway.

20 Claims, 9 Drawing Sheets

LEAD INSERTION TOOL

CROSS REFERENCE TO RELATED APPLICATIONS

This is a continuation of U.S. patent application Ser. No. 15/241,866, filed Aug. 19, 2016.

FIELD OF THE INVENTION

Aspects of the present invention relate to medical apparatus and methods. More specifically, the present invention relates to systems and methods for inserting a lead connector end of an implantable lead into an implantable pulse generator.

BACKGROUND OF THE INVENTION

Implantable pulse generators (IPGs) include, for example, pacemakers, implantable cardioverter defibrillators (ICDs), and neuromodulators or neurostimulators. Pacemakers and ICDs are used in the treatment of cardiac conditions, and neuromodulators or neurostimulators are used in chronic pain management or the actuation and control of other body systems.

Such IPGs commonly include a housing, circuitry, feedthrus, a connector assembly, and a header. The circuitry includes a hybrid and/or other electronic components that control and assess any electrical sensing and electrical stimulation associated with the electrotherapy administered by the IPG. The circuitry and a power source (e.g., a battery) are hermetically sealed in the housing.

The connector assembly is enclosed in the header, which is coupled to the housing. The connector assembly includes many internal electrically conductive components such as, for example, wires, ribbon, antennas, blocks, rings, etc. The header further includes one or more receptacles for receiving therein a lead connector end on a proximal end of an implantable lead. When a lead connector end is received in a receptacle, electrical contacts of the lead connector end are placed in electrical contact with electrical contacts (e.g., block and rings) of the connector assembly.

When the lead connector assemblies of the respective implantable leads are plugged into respective receptacles of the header, electrical pathways are established that extend from the electronics in the housing to electrodes at the distal ends of the respective implantable leads. Thus, electrical stimulation originating in the housing is led to the connector assembly through feedthrus in the housing. The connector assembly serves to transmit electrical signals out of the IPG and to each lead electrically connected to the connector assembly, the lead transmitting electrical signals between the IPG and patient tissue. Similarly, but in reverse, tissue electrical signals sensed at the lead electrodes can be transmitted through the implantable leads, the connector assembly, the feedthrus and to the electronics in the housing.

Implantable leads are becoming more flexible to address issues of lead fracture due the stiffness of implantable leads. Further, during revision cases where the implantable lead remains implanted while the IPG is replaced due to having reached its end of life or for an upgrade of the IPG, the lead becomes soft and flexible and can be hard to re-insert into the new IPG due to the lead having very little column strength. Similar issues are associated with leads employed in buried trials and then reused with a permanent IPG.

To address the lead's lack of column strength, the physician pinches the lead very close to the header while trying to advance the lead by small incremental shifts of the lead towards the header. The pinching may be via the physician's fingers or via forceps. In either case, the method takes the chance of damaging the lead. Lead damage necessitates lead replacement with a higher surgical risk, extended surgery times, and added monetary cost.

There is a need in the art for improved systems and methods of inserting a lead connector end of an implantable lead into the receptacle of an IPG header.

BRIEF SUMMARY OF THE INVENTION

Disclosed herein is lead insertion tool for inserting a lead connector end of an implantable lead into a lead receptacle of a header of an implantable pulse generator, the implantable lead including a lead body extending distally from the lead connector end. In one embodiment, the tool includes a clamshell structure including a first portion, a second portion coupled to the first portion via a hinge, an engagement mechanism, and a lead pathway configured to receive the implantable lead. Each portion of the clamshell structure includes a central structure, a leading projection extending from the central structure, and a part of a lead pathway. The part of the lead pathway of the first portion combines with the part of the lead pathway of the second portion to form the lead pathway when the first portion and second portion are abutted together when the clamshell structure is in a closed state. The lead pathway extends through the central portion and the leading projection to a free end of the leading projection. The engagement mechanism is located on at least one of the portions of the clamshell structure and includes an engaged state and a self-biasing non-engaged state. When the engagement mechanism is self-biased into the non-engaged state, the implantable lead is free to displace along the lead pathway. When the engagement mechanism is forced into the engaged state, the lead cannot displace along the lead pathway.

Depending on the embodiment, the lead pathway includes a lumen. The portions of the clamshell structure can be hinged apart to allow the implantable lead to be loaded into the lead pathway.

In one embodiment, the engagement mechanism may include an engagement member on each of the portions of the clamshell structure, the implantable lead being compressed between the engagement members when the engagement mechanism is in the engaged state and the implantable lead is located in the lead pathway. In one embodiment, at least one of the engagement members may include a hard stop that inhibits excessive compression of the implantable lead by the engagement members.

Also disclosed herein is a lead insertion tool for inserting a lead connector end of an implantable lead into a lead receptacle of a header of an implantable pulse generator, the implantable lead including a lead body extending distally from the lead connector end. In one embodiment, the tool includes a lead pathway and an engagement mechanism. The lead pathway extends through the tool and is configured to receive the implantable lead. The engagement mechanism includes an engaged state and a self-biasing non-engaged state. When the engagement mechanism is self-biased into the non-engaged state, the implantable lead is free to displace along the lead pathway. When the engagement mechanism is forced into the engaged state, the lead cannot displace along the lead pathway.

Depending on the embodiment, the lead pathway includes a lumen. The tool may include a clamshell configuration that can be opened to allow the implantable lead to be loaded into the lead pathway. The tool may include a leading projection through which the lead pathway extends. The leading projection may have an outer diameter configured to be received in the lead receptacle. The leading projection may include a tapered free end. The tool may include a trailing projection, and the lead pathway may extend from a free end of the trailing projection to a free end of the leading projection.

In one embodiment, the engagement mechanism, when in the engaged state, interacts with the implantable lead along the lead pathway between the free end of the trailing projection and the free end of the leading projection. The engagement mechanism may include at least one engagement member including an interior surface that compresses against the implantable lead when the engagement mechanism is forced into the engaged state. The engagement member may be cantilevered from a surrounding structure of the tool. The engagement member may be coupled to the surrounding tool via a living hinge.

In one embodiment, the engagement mechanism includes a pair of opposed engagement members that compress the implantable lead between the engagement members when the engagement mechanism is forced into the engaged state. In one embodiment, at least one of the engagement members includes a hard stop that inhibits excessive compression of the implantable lead by the pair of engagement members.

Also disclosed herein is method of using a lead insertion tool to insert a lead connector end of an implantable lead into a lead receptacle of a header of an implantable pulse generator, the implantable lead including a lead body extending distally from the lead connector end. The implantable lead extends through the tool such that the lead connector end projects out of a leading end of the tool and the lead body extends out of a trailing end of the tool. In one embodiment, the method includes causing the lead connector end to enter the lead receptacle by causing an engagement mechanism of the tool to engage the implantable lead while displacing the tool towards the lead receptacle with a free end of the lead connector end aligned with the lead receptacle.

In one embodiment, the tool is displaced away from the lead receptacle and along the implantable lead with the engagement mechanism disengaged from the implantable lead and then again causing the engagement mechanism of the tool to engage the implantable lead while again displacing the tool towards the lead receptacle to further drive the lead connector end into the lead receptacle. In one embodiment, the engagement mechanism self-biases out of engagement with the implantable lead.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

As can be understood from FIGS. 6-9 and discussed in detail below, implementations of the present disclosure involve a lead insertion tool 10 and associated methods of inserting a proximal end 100 of an implantable lead 105 into a lead receptacle 200 of a header 205 of an implantable pulse generator (IPG) 210 such as, for example, a pacemaker, implantable cardioverter defibrillator (ICD), neuromodulator, neurostimulator, or etc.

In one embodiment, the lead insertion tool 10 may be coupled to the lead body 110 near the proximal end 100 of the lead that is to be received in the header lead receptacle 200. The lead proximal end 100 includes, or may be in the form of, a lead connector end 115 having a number of electrical contacts 120 along the length thereof.

The tool 10 is free to slide along the lead body 110 until a lead body engagement mechanism 45 of the tool 10 is caused to engage the lead body 110, thereby fixing the tool 10 relative to the lead body 110 as long as the lead body engagement mechanism 45 is activated. The tool can then be used to insert the lead proximal end 100 into the header receptacle 200. Causing the lead connector end 120 to be fully received in the header lead receptacle 200 results in electrical contact being established between the electrical contacts 120 of the lead connector end 115 and corresponding electrical contacts inside the lead receptacle 200 that are part of a connector assembly in the IPG header 205. Via feedthrus of the IPG 210, the connector assembly of the IPG header 205 is in electrical communication with the hybrid and other electronic components of the IPG 210 hermetically sealed in the housing 215 of the IPG 210.

In one embodiment, the lead insertion tool includes a leading projection 30 through which the lead body 110 extends. The leading projection 30 is configured to facilitate guiding the lead 105 into the header lead receptacle 200 and also provide column strength to the lead body 110 to prevent its bending. In some embodiments, the leading projection 30 may serve to dilate the header lead receptacle 200 where the lead receptacle is compliant. These features, and others as described below, allow a lead proximal end 100 to be inserted into a lead receptacle 200 of an IPG header 205 in a rapid fashion with little risk of damage to the implantable lead 105 and despite the lead body 110 being highly flexible.

A. Features of the Lead Insertion Tool

Figure 1:
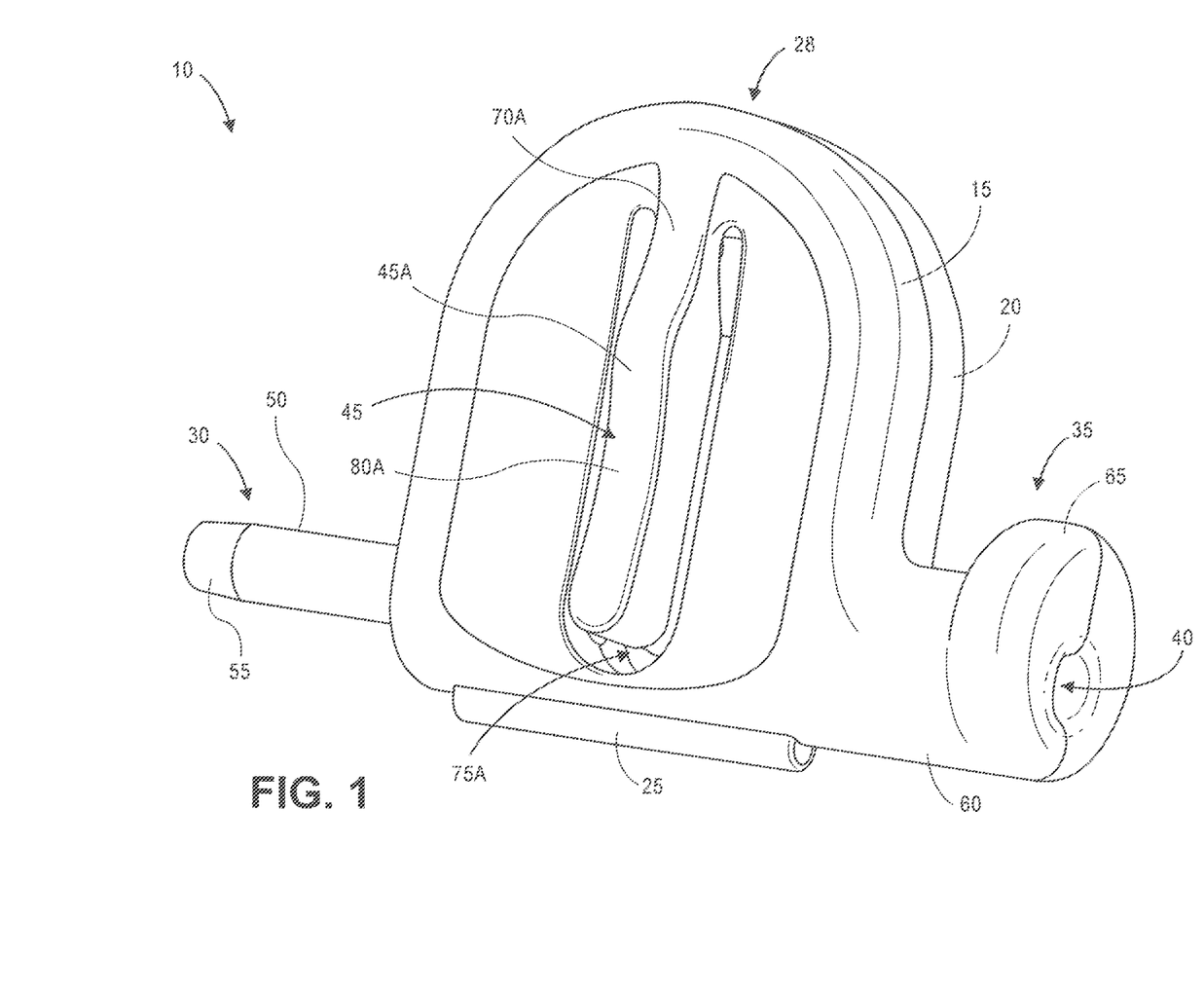
FIG. 1 is an isometric view of a lead insertion tool when its clamshell configuration is in a closed state.
Figure 2:
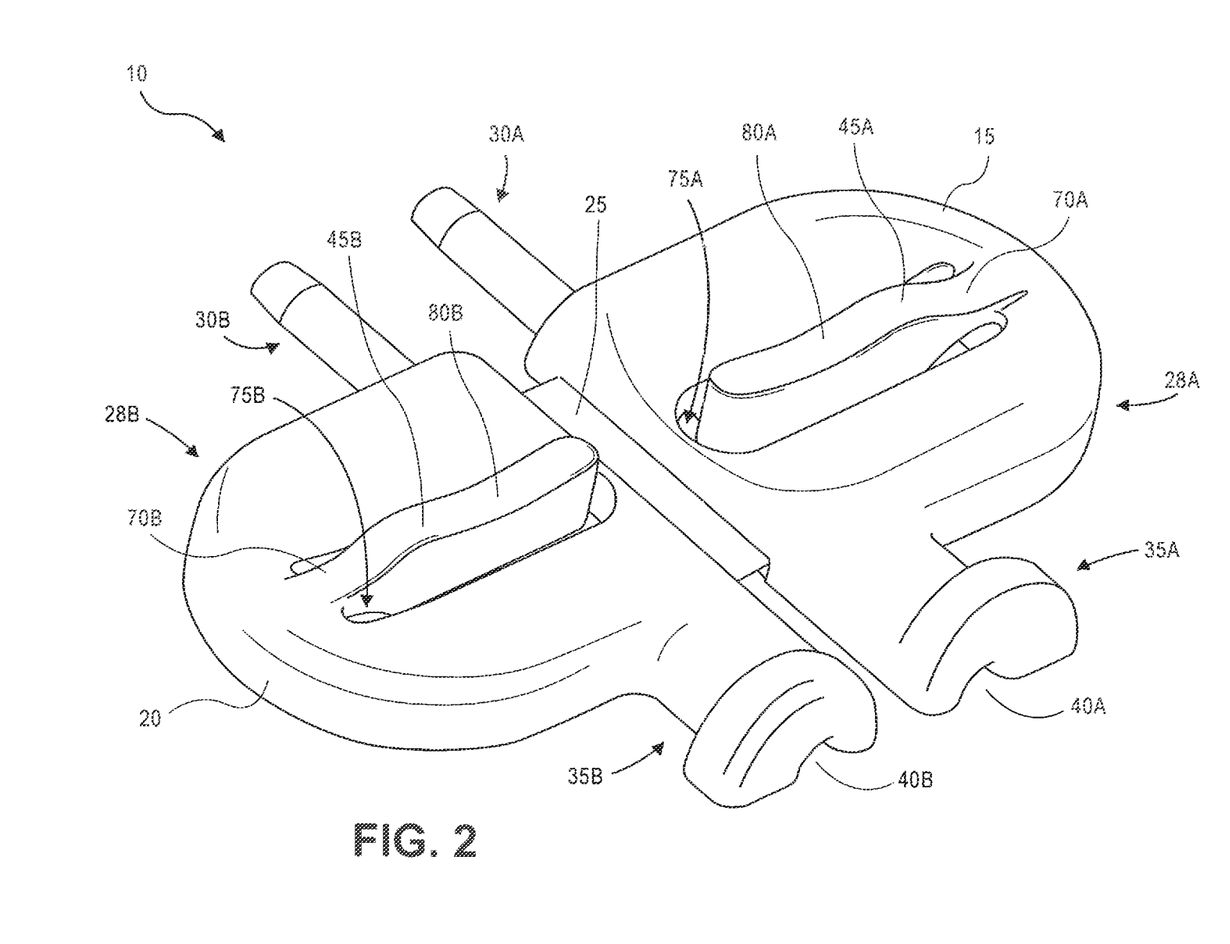
FIG. 2 is an isometric view of the lead insertion tool when its clamshell configuration is in an open state and showing its exterior.
Figure 3:
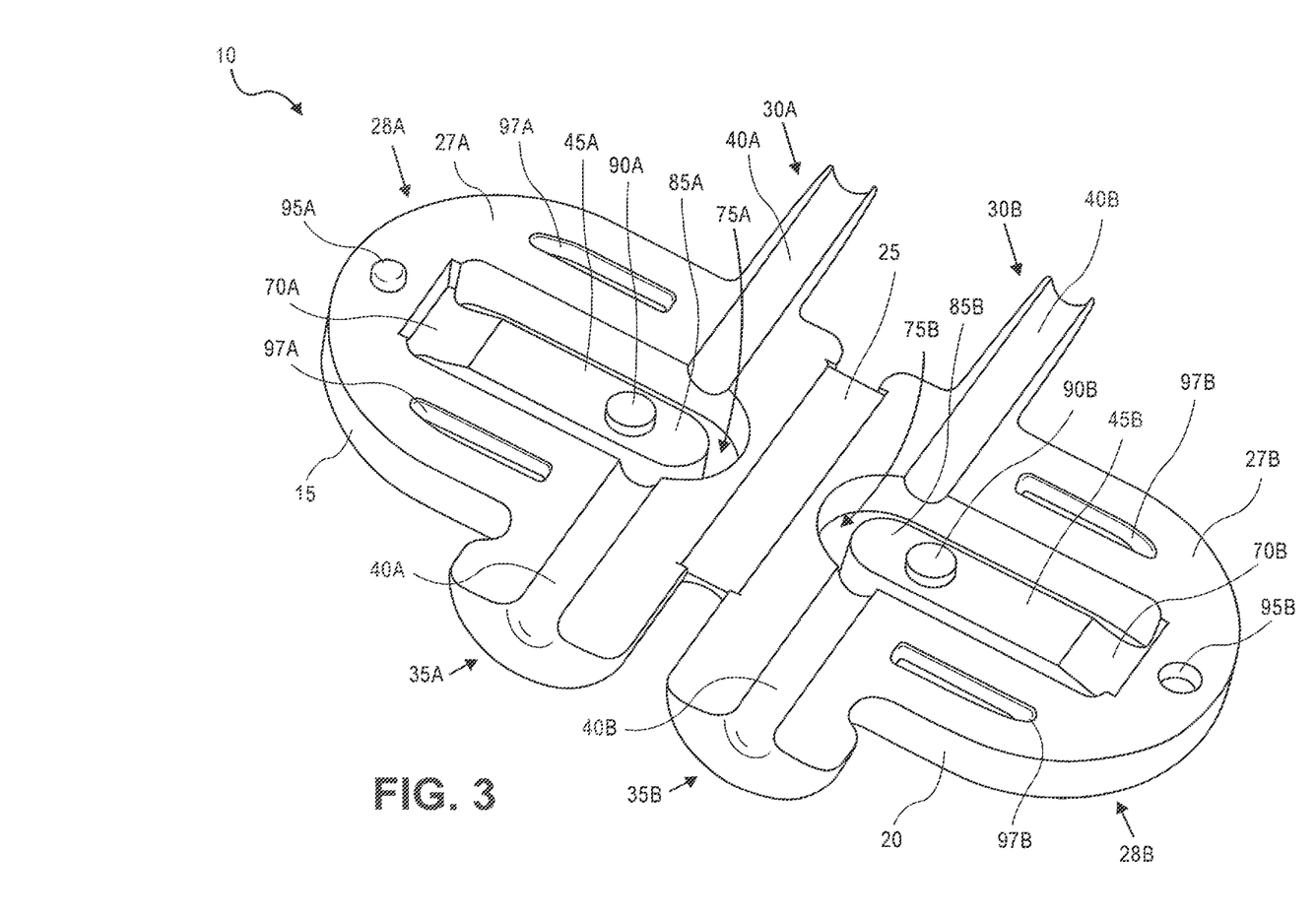
FIG. 3 is an isometric view of the lead insertion tool when its clamshell configuration is in the open state and showing its interior.

To begin a detailed discussion of an embodiment of the lead insertion tool 10, reference is made to FIGS. 1-3. FIG. 1 is an isometric view of the lead insertion tool 10 in a closed condition. FIGS. 2 and 3 are isometric views of the lead insertion tool in an open condition as viewed from the exterior and interior of the tool, respectively.

As illustrated in FIGS. 1-3, in one embodiment, the lead insertion tool 10 has a clamshell configuration including a first half 15 and a second half 20 joined by a first living hinge 25. Thus, the tool 10 can be opened such that the first half 15 and second half 20 can be separated from each other yet maintained coupled together via the living hinge 25 extending between the bottom edges of each half 15, 20, as can be understood from FIGS. 2-3. The tool 10 can then be closed such that opposed interior faces 27A, 27B (see FIG. 3) of the respective halves 15, 20 are abutted together, as indicated in FIG. 1. While a living hinge 25 is depicted in the various figures, in some embodiments, the hinge 25 can be any other type of hinge.

As shown in FIG. 1, the tool 10 further includes a central structure 28, a leading projection 30, a trailing projection 35, a hollow cylindrical shaft or lumen 40, and a lead body engagement mechanism 45. In one embodiment and as indicated in FIGS. 2-3, each of the central structure 28, leading projection 30, trailing projection 35, lumen 40, and lead body engagement mechanism 45 includes first and second portions respectively located on the first half 15 and the second half 20. Specifically, the first half 15 includes a central structure first portion 28A, a leading projection first portion 30A, a trailing projection first portion 35A, a lumen first portion 40A, and lead body engagement mechanism first portion 45A. Similarly, the second half 20 includes a central structure second portion 28B, a leading projection second portion 30B, a trailing projection second portion 35B, a lumen second portion 40B, and lead body engagement mechanism second portion 45B.

The lumen 40 may have an internal diameter of between approximately 0.03" and approximately 0.06". The leading projection 30 may have an outer diameter of between approximately 0.06" and approximately 0.09".

As depicted in FIG. 1, the leading projection 30 extends from one side of the central structure 28 in a direction opposite the trailing projection 35. The leading projection 30 includes a cylindrical outer surface 50 and a tapered free end 55. Moving along the free end 55 in a direction towards the trailing projection 35, the tapered free end 55 increases in diameter to eventually match the outer diameter of the cylindrical outer surface 50. The outer diameter of the cylindrical outer surface 50 is slightly smaller than an internal diameter of the lead receptacle 200 of the IPG header 205. As discussed below with respect to FIGS. 6-7, the leading projection 30 and its tapered free end 55 facilitate entry of the lead proximal end 100 into the header lead receptacle 200. The leading projection also gives column strength to the lead when the lead is being inserted into the header lead receptacle.

As illustrated in FIG. 1, the trailing projection 35 extends from another side of the central structure 28 in a direction opposite the leading projection 30. The trailing projection 35 includes a cylindrical outer surface 60 and a flanged free end 65. The flanged free end 65 has a diameter that is substantially greater than the outer diameter of the cylindrical outer surface 60 and, as a result, the flanged free end 65 can be grasped to displace the tool 10 distally along the lead body 110 once the lead connector end 115 is fully received in the header lead receptacle 200, as discussed below with respect to FIG. 8. Thus, the flanged free end 65 can be grasped to withdraw the tool along the lead without activating the engagement mechanism or otherwise pinching the lead.

As can be understood from FIGS. 1-3, the lumen 40 extends through the tool 10 to daylight at the free ends of each projection 30, 35. The lumen 40 is made up of lumen portions 40A, 40B defined in each respective interior face 27A, 27B. The lumen 40 is defined by a cylindrical inner surface, a portion of which is defined in each respective interior face 27A, 27B. The cylindrical inner surface has an internal diameter that is slightly larger than an outer diameter of the lead body 110, thereby allowing the lead body 110 to longitudinally displace within the lumen 40 such that the tool 10 can be moved along the lead body 110 when the lead body engagement mechanism 45 is not actuated to engage the lead body 110, as discussed below with respect to FIGS. 5 and 8.

As can be understood from FIGS. 1-3, in one embodiment, each lead body engagement mechanism portion 45A, 45B may be in the form of a member 45A, 45B that is cantilevered off of the surrounding central structure portion 28A, 28B via a living hinge 70A, 70B. As a result, each member 45A, 45B forms a peninsula from the respective central structure portion 28, 28B via the living hinge 70A, 70B, the rest of each member 45A, 45B being spaced apart from the surrounding central structure portion 28A, 28B via a void 75A, 75B defined in the surrounding central structure portion 28A, 28B. Each member 45A, 45B is located within a respective void 75A, 75B. While living hinges 70A, 70B are depicted in the various figures, in some embodiments, the hinges 70A, 70B can be any other type of hinge that may also have a biasing component (e.g., a spring) built into or supplementing the hinge.

As shown in FIGS. 1-2, the exterior of each member 45A, 45B has a contoured shape with a recess region 80A, 80B that is shaped and configured interface with a physician's thumb or index finger. Thus, the physician may actuate the lead body engagement mechanism 45 by using a thumb and index finger to squeeze the opposed members 45A, 45B inwardly such that they deflect inwardly towards each other. As discussed in detail below, the members 45A, 45B deflecting inwardly cause the members to squeeze or compress the lead body 110 between the interior surfaces 85A, 85B (see FIG. 3) of the members 45A, 45B such that the tool 10 cannot be displaced along the length of the lead body 110, thereby allowing the tool 10 to be used to insert the lead proximal end into the header lead receptacle. Thus, in one embodiment, the lead body engagement mechanism 45 may be considered a lead body compression or squeezing mechanism 45.

As indicated in FIG. 3, the interior surfaces 85A, 85B of the respective lead body engagement members 45A, 45B are immediately adjacent the paths of the lumen portions 40A, 40B. When the members 45A, 45B are not being acted upon by an outside force, such as an inwardly directed or pinching force of the physicians thumb and index finger, the members 45A, 45B assume or bias to their natural biased or non-deflected state and do not intersect the paths of the lumen portions 40A, 40B. As a result, the tool 10 is free to be slid along the length of the lead body 110 with very little, if any, resistance, as discussed below with respect to FIGS. 5 and 8.

Conversely, as can be understood from FIG. 3, the interior surfaces 85A, 85B of the respective lead body engagement members 45A, 45B intersect and extend into the paths of the lumen portions 40A, 40B when the members 45A, 45B are being acted upon by an outside force, such as an inwardly directed or pinching force of the physicians thumb and index finger. In other words, the members 45A, 45B can be forced to deflect inwardly from their natural non-deflected state to intersect the paths of the lumen portions 40A, 40B, thereby pinching or compressing the lead body 110, which is occupying the lumen 40, between the interior surfaces 85A, 85B of the respective lead body engagement members 45A, 45B. As a result, the tool 10 grasps the lead body 110 such that the tool cannot be slid along the length of the lead body 110, thereby allowing the tool 10 to be used to insert the lead proximal end 100 into the header lead receptacle 200, as discussed below with respect to FIGS. 6-7.

As shown in FIG. 3, in one embodiment, the interior surfaces 85A, 85B of the members 45A, 45B may include hard stops 90A, 90B that contact each other when the interior surfaces 85A, 85B approach each other on account of the members 45A, 45B being inwardly deflected towards each other. The hard stops 90A, 90B may be sized to prevent the interior surfaces 85A, 85B from contacting each other, thereby leaving a gap or space between the interior surfaces when the members are fully inwardly deflected towards each other such that the hard stops abut each other. This hard stop feature helps to prevent the physician from overly pinching the lead body 110 between the member interior surfaces 85A, 85B and damaging the lead body. Thus, in part due to the hard stops, the physician can be assured of sufficient compression on the lead body to assure desired displacement and manipulation of the of the lead body while minimizing the risk of lead body damage due to over compression of the lead body.

As illustrated in FIG. 3, in one embodiment, the interior face 27A of the first half 15 includes a male locking feature 95A (e.g., a pin, tab, etc.) that is received in a female locking feature 95B (e.g., hole, recess, etc.) of the interior face 27B of the second half 20 in an interference fit arrangement such that the locking features 95A, 95B work together to keep the halves 15, 20 in a closed state, as depicted in FIG. 1. The locking strength of the locking features 95A, 95B can easily be overcome by the physician intentionally prying the halves 15, 20 apart by, for example, inserting a tool, finger nail, etc. between the interior faces 27A, 27B of the halves 15, 20.

As shown in FIG. 3, male alignment features 97A (e.g., ridges, pins, etc.) may also be present on the interior face 27A of the first half 15 to be receive by corresponding female alignment features 97B (e.g., slots, troughs, holes, etc.) defined in the interior face 27B of the second half 20. These features 97A, 97B mating with each other will facilitate the locking features 95A, 95B aligning properly and the lumen portions 40A, 40B properly aligning to define a cylindrical lumen 40 from free end to free end of the projections 30, 35.

Depending on the embodiment, the tool 10 and its various components may be made from a variety of materials such as, for example, Polypropylene (PP), Polyethylene (PE), Acrylonitrile Butadiene Styrene (ABS), etc. Depending on the embodiment, the tool 10 may be disposable or capable of being sterilized and reused.

With the preceding understanding of the various aspects of the lead insertion tool 10, the discussion will now turn towards methods of employing the tool.

B. Method of Using the Lead Insertion Tool

Figure 4:
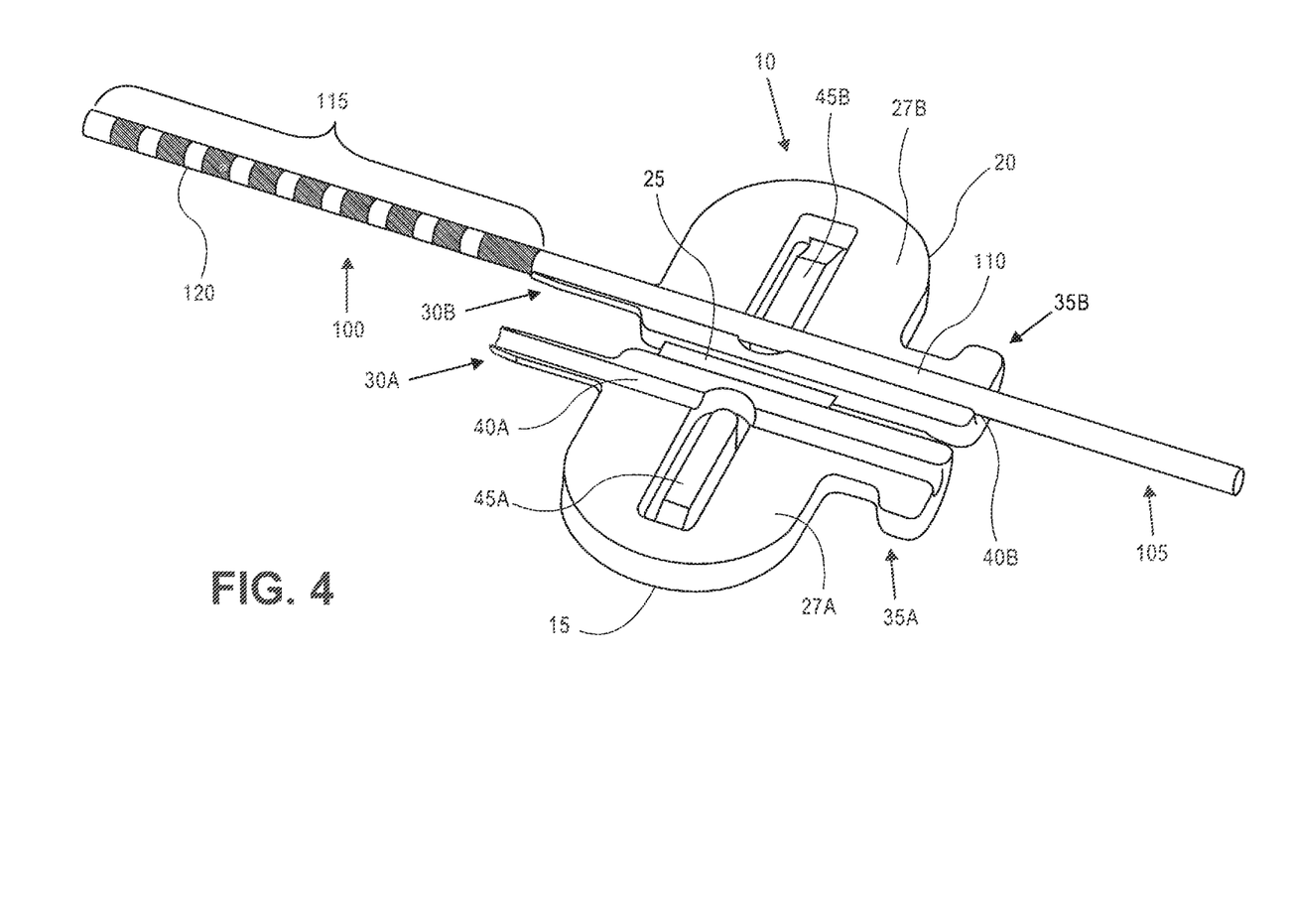
FIG. 4 is a similar view of lead insertion tool as depicted in FIG. 3, except also depicting a proximal region of an implantable lead being located in one-half of a lead receiving channel of the lead insertion tool.

FIG. 4 is an isometric view of the lead insertion tool 10 and proximal region 100 of the implantable lead 105, wherein the lead is being loaded into the tool. As shown in FIG. 4, the clamshell configuration of the tool 10 is open such the opposed interior surfaces 27A, 27B of the halves 15, 20 are spaced apart from each other and the halves 15, 20 are nearly flat relative to each other. Also, the proximal end 100 of the implantable lead 105 is positioned relative to the tool 10 such that the lead body 110 just distal the distal edge of the lead connector end 115 is received in the lumen second portion 40B.

Figure 5:
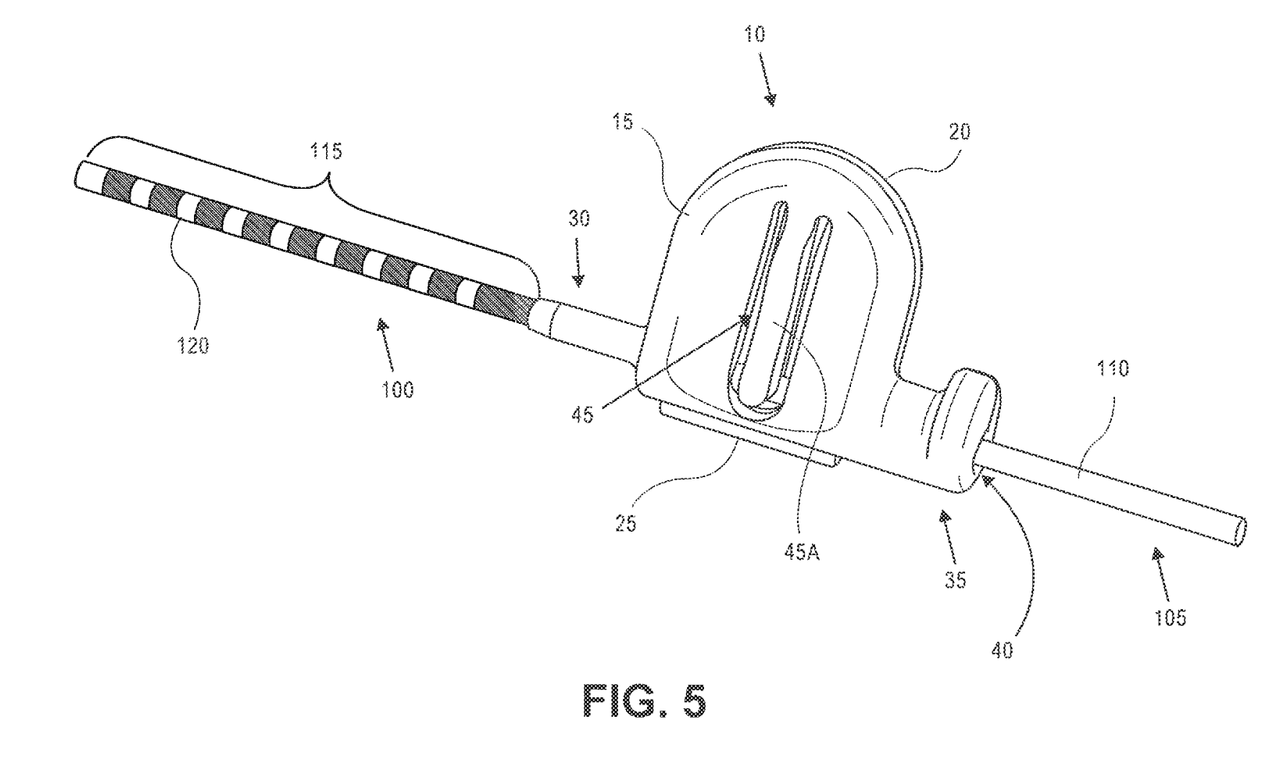
FIG. 5 is the same view as FIG. 4, except the clamshell configuration of the lead insertion tool has been closed about the lead body such that the lead occupies the lead receiving channel of the lead insertion tool.

FIG. 5 is the same view as FIG. 4, except the clamshell configuration of the lead insertion tool 10 has been closed about the lead body 110 such that the lead 105 occupies the lead receiving channel or lumen 40 of the lead insertion tool 10 between the free ends of the projections 30, 35. The entirety of the lead connector end 115 extends from the free end of the leading projection 30.

As can be understood from FIGS. 3 and 5, when the clamshell configuration of the tool 10 is in the closed state about the lead body 110, the interior surfaces 27A, 27B abut each other, the alignment features 97A, 97B interface, and the locking features 95A, 95B are engaged to maintain the halves 15, 20 in a closed state. Also, the interior surfaces 85A, 85B of the lead body engagement members 45A, 45B are located immediately adjacent the exterior surface of the lead body 110. As explained above, the members 45A, 45B self-bias to a position where the interior surfaces 85A, 85B will not contact the exterior surface of the lead body 110. Thus, since the members 45A, 45B have not yet been subjected to an inward force (e.g., via being pressed inward by the physician's thumb and index finger), the interior surfaces 85A, 85B do not yet contact the exterior surface of the lead body 110. Because the engagement members 45A, 45B have not been forced to engage the lead body 110 and, as noted above, the lumen 40 is of a greater diameter than the lead body 110, the tool 10 can be freely displaced along the lead body 110.

Figure 6:
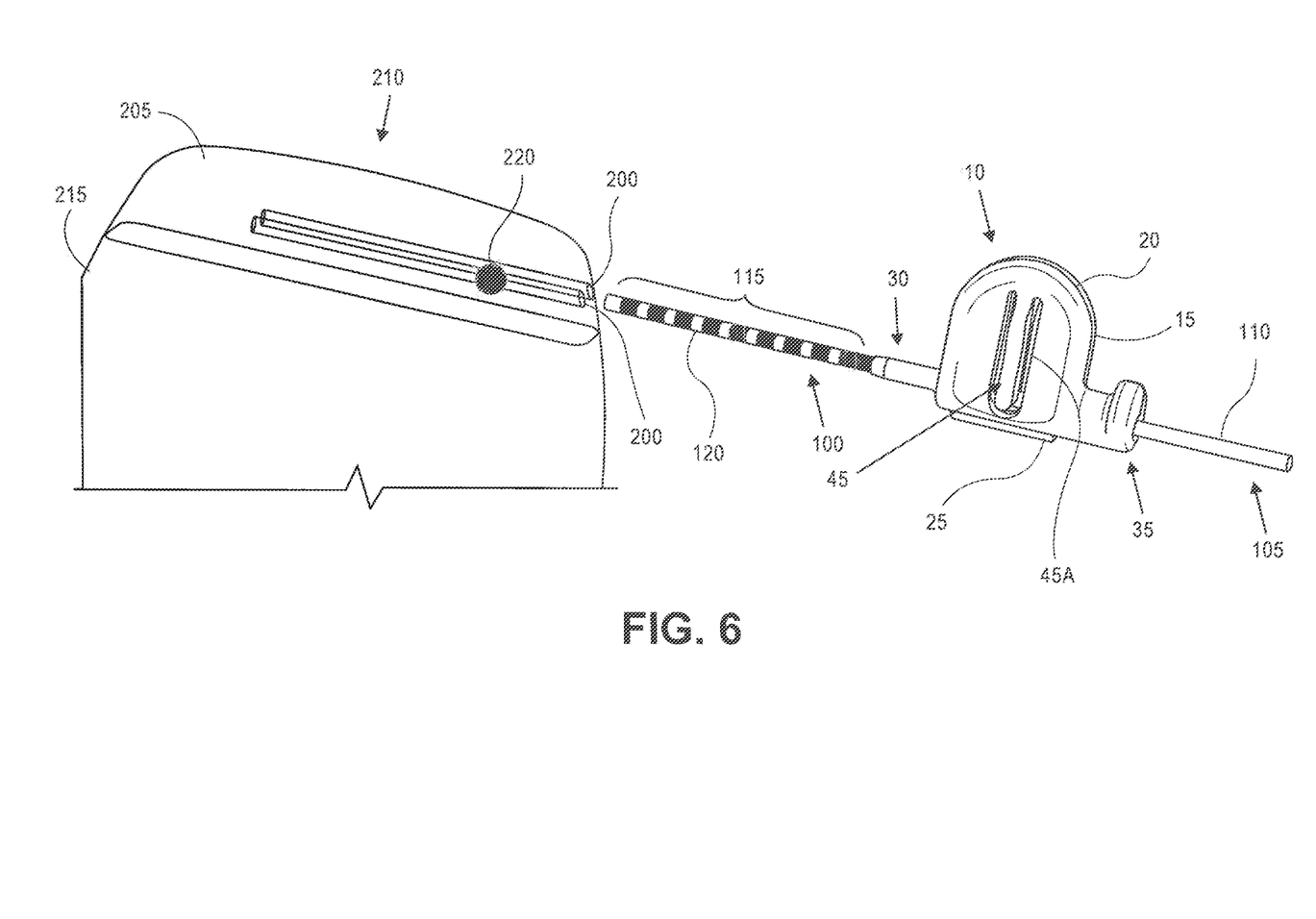
FIG. 6 shows the lead and lead insertion tool in the same relationship depicted in FIG. 5, except the lead proximal end is being aligned with a lead receptacle of a header of an IPG.

FIG. 6 shows the lead 105 and lead insertion tool 10 in the same relationship depicted in FIG. 5, except the lead proximal end 100 is being aligned with the lead receptacle 200 of the header 205 of the IPG 210, and the lead engagement mechanism 45 is being actuated to engage the lead body 110. Specifically, inward forces are being applied (e.g., via a pinching action of the physician's thumb and index finger) to each engagement member 45A, 45B to drive the members 45A, 45B inward. As a result, the interior surfaces 85A, 85B of the lead body engagement members 45A, 45B compress or pinch the lead body 110, thereby preventing displacement of the tool 10 along the lead body 110 and allowing the tool 10 to be used to insert the lead connector end 115 into the appropriate header lead receptacle 200.

Figure 7:
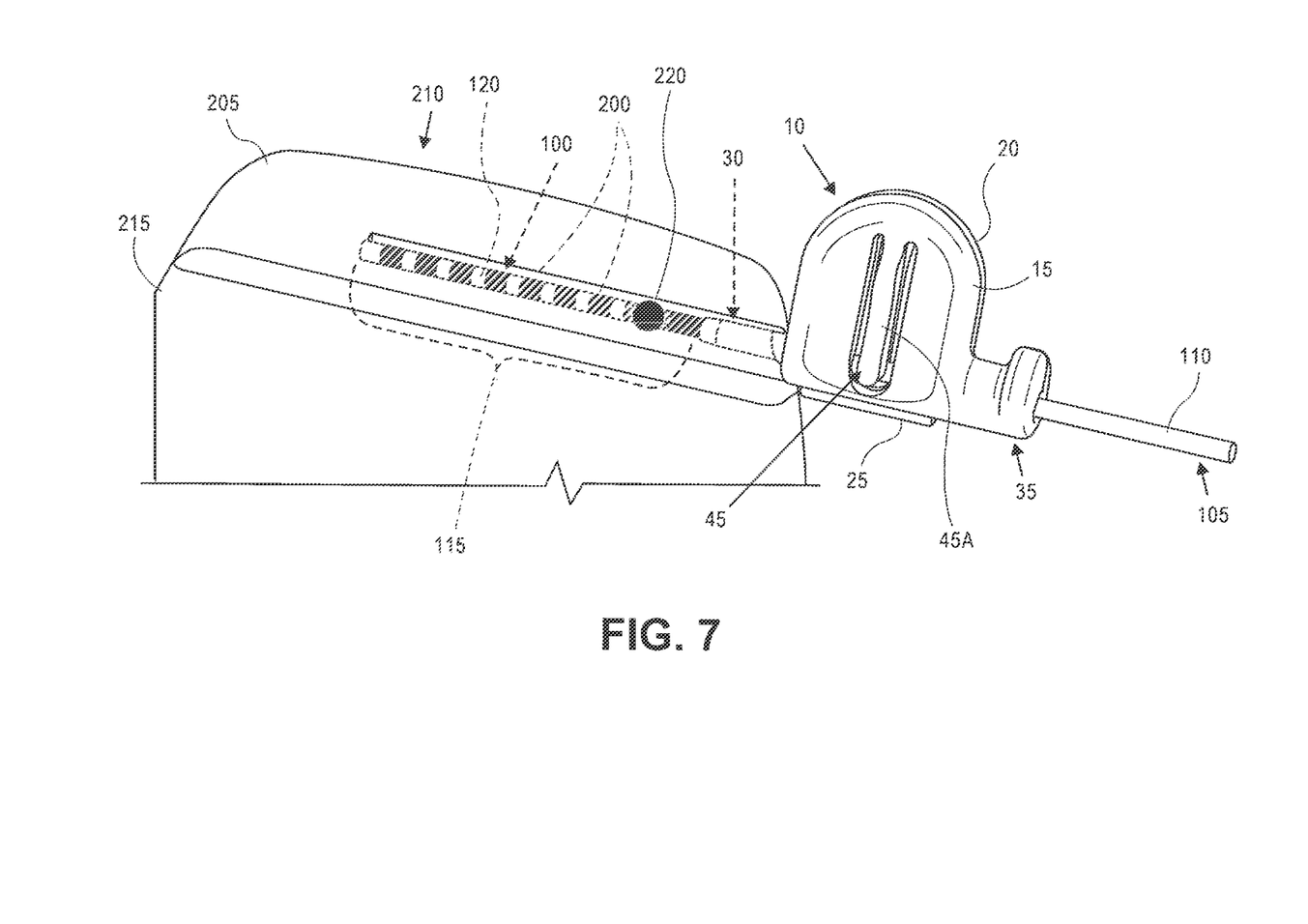
FIG. 7 illustrates the lead proximal end received in the lead receptacle of the header via insertion by the lead insertion tool.

FIG. 7 illustrates the lead proximal end 100 received in the lead receptacle 200 of the header 205 via insertion by the lead insertion tool 10. As can be understood from FIG. 7, the leading projection 30 of the tool 10 has also been received in the header lead receptacle 200. The lead body engagement mechanism 45 of the tool 10 will have been in compressing or pinching engagement with the lead body 110 to allow the lead connector end 115 to be fully received in the header lead receptacle 200 as indicated in FIG. 7. As noted above, in one embodiment, the leading projection 30 has a tapered tip and an outer diameter that exceeds the inner diameter of the header lead receptacle 200 such that the leading projection 30 can dilate the header lead receptacle 200 where the receptacle 200 is of a compliant configuration. In one embodiment, this nature of the leading projection 30 can be employed to step-by-step and incrementally feed the lead connector end 115 into the receptacle 200 by starting out with the free end of the leading projection 30 being generally even with the free proximal end of the lead connector end 115 and inserting the lead connector end 115 the length of the leading projection 30. The engagement mechanism 45 of the tool 10 can then be released and the tool distally displace along the length of the lead body 110 until the leading projection 30 is outside the receptacle 200. The engagement mechanism 45 can then be reengaged with the lead body 110 and proximally displaced the length of the leading projection 30 to further incrementally insert the lead connector end 115 in to the header lead receptacle 200. This process can be repeated over and over until the lead connector end 115 is fully received in the receptacle 200 as indicated in FIG. 7.

As can be understood from FIG. 7, a setscrew 220 on the IPG header 205 may be tightened down on the lead connector end 115 before the tool 10 is withdrawn from the header lead receptacle 200 and the fully inserted lead connector end. This will prevent the lead connector end from inadvertently being withdrawn from the header lead receptacle.

Figure 8:
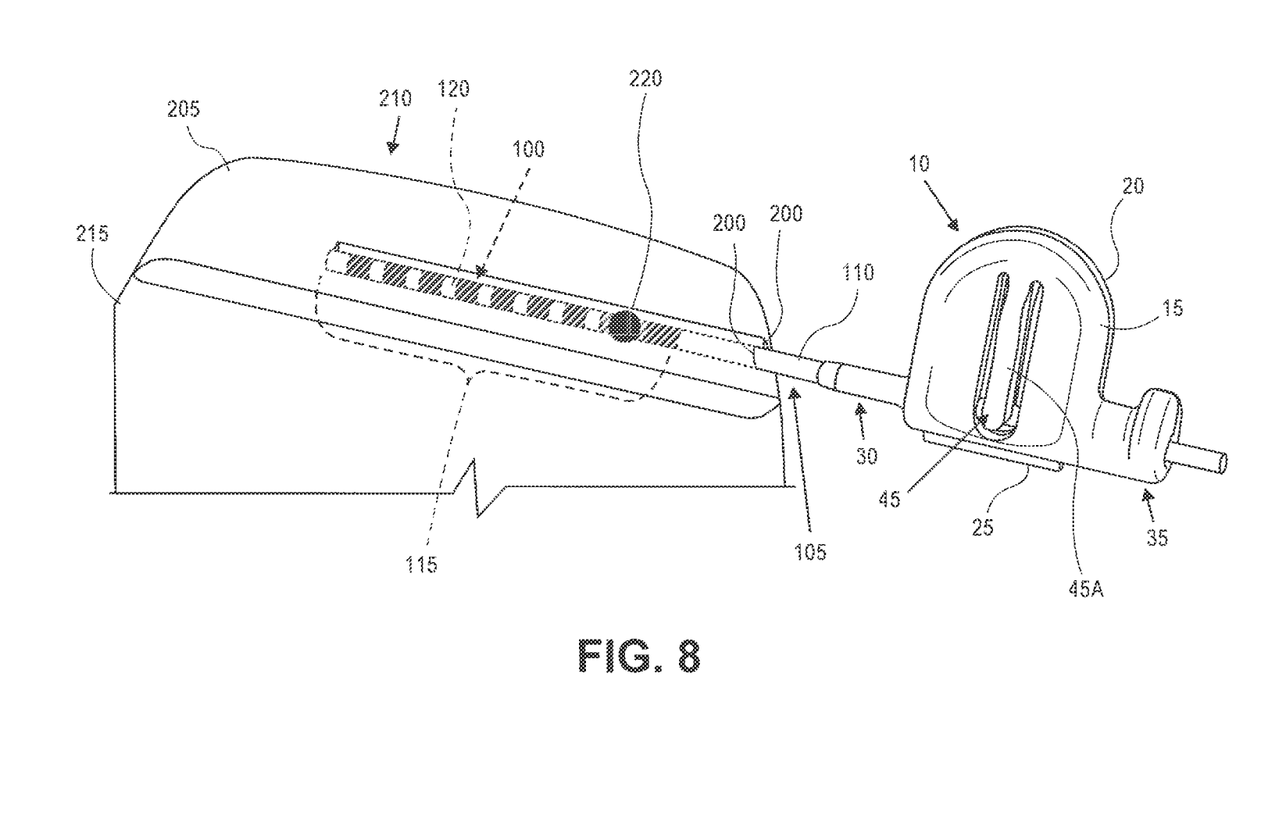
FIG. 8 depicts the lead insertion tool being distally withdrawn along the lead with the lead proximal end continuing to be received in the lead receptacle.

FIG. 8 depicts the lead insertion tool 10 being distally withdrawn along the lead body 110 with the lead proximal end 100 continuing to be received in the lead receptacle 200. Specifically, the physician no longer pushes the members 45A, 45B inward into engagement with the lead body 110, instead allowing the members 45A, 45B to self-bias outwardly and out of engagement with the lead body 110. Because the engagement members 45A, 45B are no longer being forced to engage the lead body 110 and, as noted above, the lumen 40 is of a greater diameter than the lead body 110, the tool 10 can be freely distally displaced along the lead body 110 such that the leading projection 30 is caused to exit the header lead receptacle 200, leaving the lead connector end 115 fully received in the header lead receptacle 200.

Figure 9:
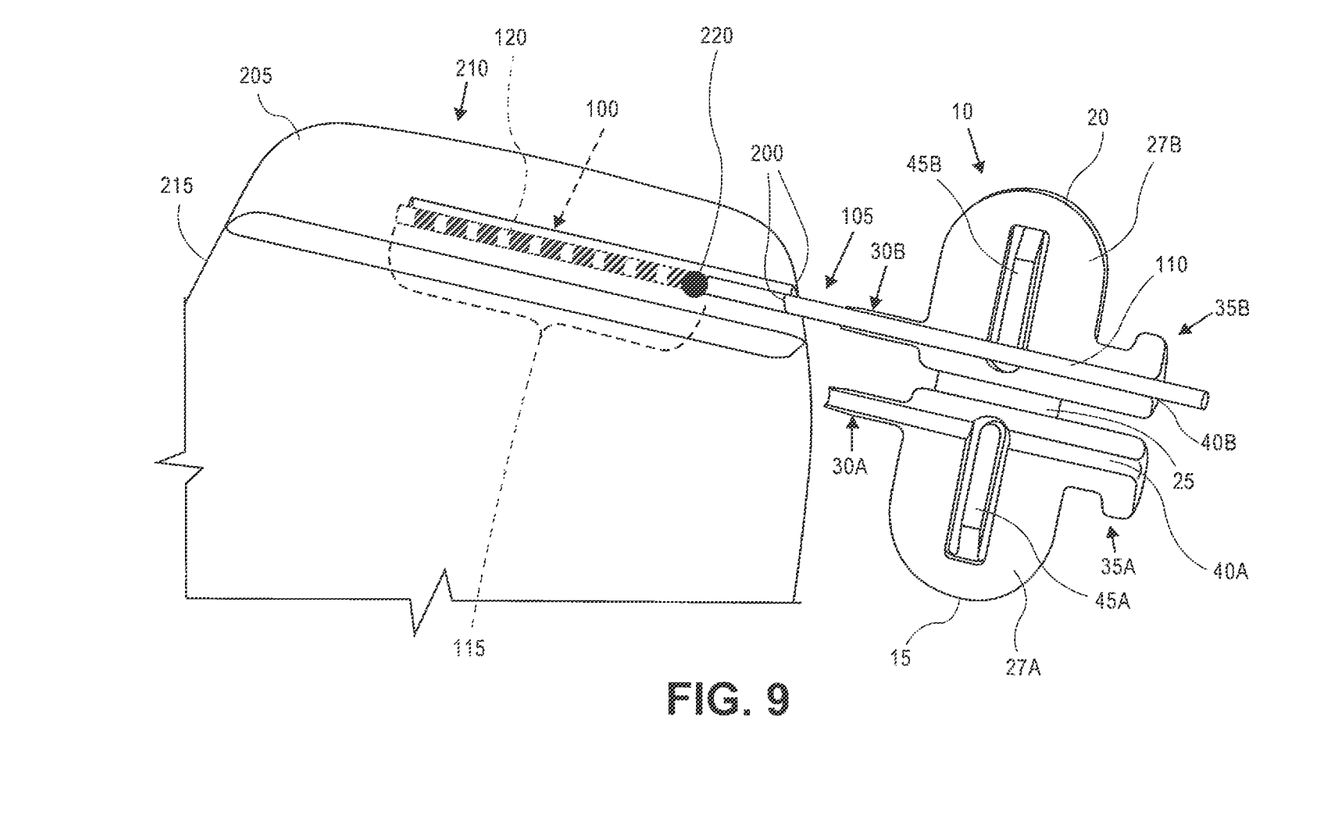
FIG. 9 shows the clamshell configuration of the lead insertion tool being opened and the lead insertion tool being removed from about the proximal region of the lead.

FIG. 9 shows the clamshell configuration of the lead insertion tool 10 being opened and the lead insertion tool 10 being removed from about the lead 105. The lead connector end 115 is still fully received in the header lead receptacle 200. The tool 10 can then be reused in a similar manner to insert a second lead connector end into the second header lead receptacle 200 illustrated in FIG. 9.

As can be understood from the preceding discussion, the tool 10 provides column strength to the lead where it is most needed when the lead is being inserted into the header lead receptacle. Also, the tool grips the lead without crushing it. The tool can also slide along the lead when the engagement mechanism is self-biased into its non-engaged state, yet solidly engages the lead when forced out of the self-biased non-engage state into the engaged state by the physician squeezing together the engagement members. The tool is inexpensive to manufacture. The tool lumen can be sized to work with a wide variety of lead body diameters. Finally, the tool is simple and intuitive to use.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A lead insertion tool for facilitating the insertion of an implantable lead into a header of a pulse generator, the lead insertion tool comprising:
    a body having a first member and a second member, wherein each member including an upper portion and a lower portion,
    a hinge connecting the lower portions of the first member and the second member, the hinge biased to separate the first member from the second member, the hinge configured to facilitate a mating of the first member with the second member in response to compressive forces to each of the first and second members;
    a first elongated tab having a first end and a second end, the first end of the first elongated tab hingley connected to the upper portion of the first member, the first tab extending towards the lower portion of the first member;
    a second elongated tab having a first end and a second end, the first end of the second elongated tab hingley connected to the upper portion of the second member, the second tab extending towards the lower portion of the second member;
    an elongated lead pathway, formed when the first member is in a mated state with the second member, the lead pathway including a first portion positioned proximate to the lower portion of the first member, and a second portion positioned proximate to the lower portion of the second member, wherein the elongated lead pathway, first elongated tab and second elongated tab are configured such that a lead positioned within the elongated lead pathway is movable along the elongated lead pathway when the first member and the second member are in the mated state and the first elongated tab and the second elongated tab are in a non-engaged state; and
    wherein in response to a compressive force on the second ends of each of the first and second elongated tabs with the first member and the second member in the mated state, the first elongated tab and the second elongated tab are configured to hingley deflect inwards toward the elongated lead pathway and engage the lead positioned within the elongated lead pathway to inhibit movement of the lead along the elongated lead pathway.

2. The lead insertion tool of claim 1, and further including a first protrusion positioned proximate the second end of the first tab and a second protrusion positioned proximate the second end of the second tab, wherein the first and second protrusions are positioned such that subsequent to the mating of the first member with the second member and the placement of the lead within the lead pathway, and when the user applies the compressive force to the second ends of each of the first and second elongated tabs, the first and second protrusions are positioned respectively to engage each other to limit the compression of the first and second elongated tabs on the lead.

3. The lead insertion tool of claim 1, wherein the first member includes a protrusion and wherein the second member includes a recess, wherein the protrusion and the recess each being positioned and shaped to facilitate the alignment of the mating of the first and second members such that the recess receives therein the protrusion.

4. The lead insertion tool of claim 2, wherein the first member includes a third protrusion and wherein the second member includes a recess, wherein the third protrusion and the recess each being positioned and shaped to facilitate the alignment of the mating of the first and second members such that the recess receives therein the third protrusion.

5. The lead insertion tool of claim 1, wherein the hinge connecting the first member to the second member is a living hinge.

6. A lead insertion tool for facilitating the insertion of an implantable lead into a header of a pulse generator, the lead insertion tool comprising:
a body having a first portion and a second portion, the first portion having a curved edge and a straight edge distal the curved edge, and the second portion having a curved edge and a straight edge distal the curved edge;
a hinge connecting the straight edge of first portion of the body to the straight edge of the second portion of the body, the hinge biased to separate the first portion of the body from the second portion of the body, the hinge configured to facilitate a mating of the first portion with the second member portion in response to compressive forces to each of the first and second portions;
a first elongated tab having a first end and a second end, the first end of the first elongated tab hingley connected to the first portion of the body proximate to the curved edge of the first portion of the body, the first tab extending towards the straight edge of the first portion of the body with the second end of the first tab positioned proximate the straight edge of the first portion of the body;
a second elongated tab having a first end and a second end, the first end of the second elongated tab hingley connected to the second portion of the body proximate to the curved edge of the second portion of the body, the second tab extending towards the straight edge of the second portion of the body with the second end of the second tab positioned proximate the straight edge of the second portion of the body;
an elongated lead pathway formed when the first portion of the body is in a mated state with the second portion of the body, the elongated lead pathway including a first portion positioned proximate to and parallel with the straight edge of the first portion of the body and a second portion positioned proximate to and parallel with the straight edge of the second portion of the body, wherein the elongated lead pathway, first elongated tab and second elongated tab are configured to allow movement of a lead positioned within the elongated lead pathway with the first member and the second member in the mated state and the first elongated tab and the second elongated tab are in a non-engaged state; and
wherein in response to a compressive force on the second ends of each of the first and second elongated tabs with the first member and the second member in the mated state, the first elongated tab and the second elongated tab are configured to hingley deflect inwards toward the elongated lead pathway and engage the lead positioned within the elongated lead pathway to inhibit movement of the lead along the elongated lead pathway.

7. The lead insertion tool of claim 6, and further including a first protrusion positioned proximate the second end of the first tab and a second protrusion positioned proximate the second end of the second tab, wherein the first and second protrusions are positioned such that subsequent to the mating of the first portion of the body with the second portion of the body and the placement of the lead within the lead pathway, and when the user applies the compressive force to the second ends of each of the first and second elongated tabs, the first and second protrusions are positioned respectively to engage each other to limit the engagement of the first and second elongated tabs on the lead.

8. The lead insertion tool of claim 6, wherein the first portion of the body includes a protrusion and wherein the second portion of the body includes a recess, wherein the protrusion and the recess each being positioned and shaped to facilitate the alignment of the mating of the first and second portions of the body such that the recess receives therein the protrusion.

9. The lead insertion tool of claim 7, wherein the first portion of the body includes a third protrusion and wherein the second portion of the body includes a recess, wherein the third protrusion and the recess each being positioned and shaped to facilitate the alignment of the mating of the first and second portions of the body such that the recess receives therein the third protrusion.

10. The lead insertion tool of claim 6, wherein the hinge connecting the first portion of the body to the second portion of the body is a living hinge.

11. A lead insertion tool for facilitating insertion of an implantable lead into a pulse generator, the lead insertion tool comprising:
a body having a first member and a second member, wherein each member includes an upper portion and a lower portion;
a hinge connecting the lower portions of the first member and the second member, the hinge biased to separate the first member from the second member;
a locking mechanism configured to hold the first member and the second member in a mated state, wherein the first member and the second member form an elongated lead pathway therebetween in the mated state;
a first elongated tab having a first end and a second end, wherein the first end of the first elongated tab is hingley connected to the upper portion of the first member and the second end of the first elongated tab is at least partially adjacent to the elongated lead pathway;
a second elongated tab having a first end and a second end, wherein the first end of the second elongated tab is hingley connected to the upper portion of the second member and the second end of the second elongated tab is at least partially adjacent to the elongated lead pathway;
wherein the elongated lead pathway, first elongated tab and second elongated tab are configured such that a lead positioned within the elongated lead pathway is movable along the elongated lead pathway when the first member and the second member are in the mated state and the first elongated tab and the second elongated tab are in a non-engaged state; and
wherein the first elongated tab and the second elongated tab are configured to deflect inwardly in an engaged state and intersect the elongated lead pathway such that the first elongated tab and the second elongated tab engage the lead positioned within the elongated lead pathway to inhibit movement of the lead along the elongated lead pathway.

12. The lead insertion tool of claim 11, wherein the second end of the first elongated tab is at least partially adjacent to a first side of the elongated lead pathway and wherein the second end of the first elongated tab is configured in the engaged state to deflect inwardly to intersect the first side of the elongated lead pathway; and
wherein the second end of the second elongated tab is at least partially adjacent to a second opposing side of the elongated lead pathway and wherein the second end of the second elongated tab is configured in the engaged state to deflect inwardly to intersect the second opposing side of the elongated lead pathway.

13. The lead insertion tool of claim 11, wherein an exterior side of the first elongated tab and an exterior side of the second elongated tab are compressed inwardly in the engaged state such that an interior side of the first elongated tab and an interior side of the second elongated tab engage the lead positioned within the elongated lead pathway to inhibit movement of the lead along the elongated lead pathway.

14. The lead insertion tool of claim 11, wherein the elongated lead pathway is formed with an internal diameter that is greater than an outer diameter of the lead positioned within the elongated lead pathway such that the lead positioned within the elongated lead pathway is movable along the elongated lead pathway when the first member and the second member are in the mated state and the first elongated tab and the second elongated tab are in the non-engaged state.

15. The lead insertion tool of claim 11, wherein the first end of the first elongated tab is hingley connected to the upper portion of the first member by a living hinge and the second end of the first elongated tab forms a peninsula within a first void formed in the first member; and
wherein the first end of the second elongated tab is hingley connected to the upper portion of the second member by a living hinge and the second end of the second elongated tab forms a peninsula within a second void formed in the second member.

16. The lead insertion tool of claim 15, wherein the second end of the first elongated tab in the engaged state is configured to deflect at least partially through the first void to engage a first side of the lead positioned in the elongated lead pathway; and
wherein the second end of the second elongated tab in the engaged state is configured to deflect at least partially through the second void to engage a second side of the lead positioned in the elongated lead pathway.

17. The lead insertion tool of claim 11, and further including a first protrusion positioned proximate the second end of the first elongated tab and a second protrusion positioned proximate the second end of the second elongated tab, wherein when the first member and the second member are in the mated state and the first elongated tab and the second elongated tab are in the engaged state, the first and second protrusions are positioned to engage each other to limit compression by the first and second elongated tabs on the lead positioned in the elongated lead pathway.

18. The lead insertion tool of claim 11, wherein the locking mechanism configured to hold the first member and the second member in the mated state, comprises:
a male locking feature on an interior face of the first member; and
a female locking feature on an interior face of the second member, wherein the female locking feature is positioned to receive the male locking feature in an interference fit arrangement to maintain the first and second members in the mated state.

19. The lead insertion tool of claim 11, further comprising:
a leading projection extending from a first side of the first member and the second member in the mated state and configured to form an extension of the elongated lead pathway, wherein the leading projection, wherein the leading projection includes:
a tapered free end with a cylindrical outer surface, wherein an outer diameter of the cylindrical outer surface at a first side adjacent to the first member and the second member is slightly smaller than an internal diameter of a lead receptacle of the pulse generator; and
wherein the outer diameter of the cylindrical outer surface decreases from the first side adjacent to the first member and the second member in the mated state to a second side extending outwards.

20. The lead insertion tool of claim 19, further comprising:
a trailing projection extending from an opposite, second side of the first member and the second member in the mated state, wherein the trailing projection is configured to form another extension of the elongated lead pathway and further includes:
a flanged free end with an outer diameter substantially greater than the elongated lead pathway.

* * * * *